United States Patent [19]

Granados

[11] Patent Number: 4,973,667
[45] Date of Patent: Nov. 27, 1990

[54] BACULOVIRUS PROTEINS AND VIRAL PESTICIDES CONTAINING SAME

[75] Inventor: Robert R. Granados, Ithaca, N.Y.

[73] Assignee: Boyce Thompson Institute for Plant Research, Inc., Ithaca, N.Y.

[21] Appl. No.: 426,795

[22] Filed: Oct. 25, 1989

Related U.S. Application Data

[63] Continuation-in-part of Ser. No. 178,259, Apr. 6, 1988.

[51] Int. Cl.$^5$ .................. C07K 15/02; C07K 15/04
[52] U.S. Cl. ................................ 530/350; 514/21; 424/89
[58] Field of Search .................. 530/350, 395; 514/21

[56] References Cited

PUBLICATIONS

Yamamoto et al., 1978, Journal of Invertebrate Pathology 31:48–56.
Lewis; R., 1989, *Genetic Engineering News*, "Baculoviruses Prove Valuable in Vaccines, and Biopesticides" 9(7):1, 34 and 35.
Derksen et al. 1988 *Virology* 167:242–250.
Hamm, J. 1982 *Environmental Entomology* 11(1):159–160.
Shapiro et al. 1987 *J. Econ. Entomol.* 80(6): 1113–1116.
Shields, K. S. 1984 Diss. Abstracts Intern. 45/04–8, p. 1109 (abstract).
Adang, M. J. 1981 Diss. Abstracts Intern. 42/05–8, p. 1754 (abstract).
Adang et al. 1983 Comp Biochem Physiol A Comp Physiol., 75(2):233–238, (abstract).
Adang et al. 1981 Cell Tissue Res. 218(1): 141–147, (abstract).
Tanada et al. J. Invertebr. Pathol. 45, 125–138 (1985).
Falcon, F. A. Proc. 3rd Intern. Colloq. Invertebr. Pathol. Brighton, UK, pp. 125–128 (1982).

*Primary Examiner*—Margaret Moskowitz
*Assistant Examiner*—Keith C. Furman
*Attorney, Agent, or Firm*—C. Harold Herr

[57] ABSTRACT

Nuclear polyhedrosis viruses, for example, *Autographa californica* nuclear polyhedrosis virus (AcMNPV), useful in the control of lepidopterous larvae such as the larvae of the cabbage looper *Trichoplusia ni*, have been found to have enhanced infectivity when mixed with certain proteins obtained from the granulin fraction of *Trichoplusia ni* granulosis virus (TnGV) or *Heliothis armigera* granulosis virus (HaGV), and from the polyhedrin fraction of AcMNPV viruses. The proteins from the TnGV granulin fraction have molecular weights of about 101 and about 104 kd. The enhanced infectivity is correlated to biochemical and structural changes in the *T.ni* peritrophic membrane.

7 Claims, No Drawings

BACULOVIRUS PROTEINS AND VIRAL PESTICIDES CONTAINING SAME

This application is a continuation-in-part of my co-pending application filed Apr. 6, 1988 as Ser. No. 07/178,259.

FIELD OF THE INVENTION

The invention relates to new baculovirus proteins, baculovirus pesticides containing them, their preparation, and use. More particularly, the invention relates to pest control compositions effective against insect pests and particularly against lepidopterous larvae comprising a nuclear polyhedrosis virus and a viral-coded protein factor which enhances infectivity and speed of kill.

BACKGROUND OF THE INVENTION

The development and use of microbial agents as alternatives to chemicals for controlling noxious insect population has attracted increased attention and interest in recent years because of the public's increased awareness in maintaining the quality of the environment. The accumulation of pesticide residues in air, soil, water, and animals has helped to bring this heightened interest about. The insect pathogens in the family Baculoviridae, by virtue of their specificity, virulence, and safety for non-target species, have become logical candidates in this regard.

Several baculoviruses have been registered with the United States Environmental Protection Agency for use in the United States. Of the baculovirus products registered by the EPA, at least one, Elcar, the *Heliothis zea* nucleopolyhedrosis virus, was commercialized by Sandoz. Others which are registered for use under the auspices of the USDA Forest Service include Gypchek for control of the gypsy moth, *Lymantria dispar*, and TM-Bicontrol-1, for use against the Douglas-fir tussock moth, *Orgyia pseudotsugata*. A baculovirus product, Neochek S, has been used in Europe for control of the European pine sawfly, *Neodiprion sertifer*.

The development of viral insecticides has been patterned after conventional pesticidal use and technology, and this, in turn, has led in part at least to less than expected results when viral insecticides are used as substitutes for chemical pesticides. There are many factors to consider for effective use of insecticides; the size and age of the insect population, the time of day, and the means of application. There is also an education problem. Farmers like to see insects die immediately after treatment, and unmodified baculovirus insecticides usually take 5–7 days to kill. Failure to bring pest population below the economic threshold along with lack of quickness of kill are two of the main deficiencies of viral pesticides.

SUMMARY OF THE INVENTION

The present invention overcomes some of the problems described above and satisfies all of the requirements for a safe, effective, and inexpensive insecticide by providing baculovirus pest control compositions having enhanced viral infectivity and speed of kill. Such compositions comprise a nuclear polyhedrosis virus, e.g. *Autographa california* (ACMNPV) and a protein purified from the granulin fraction of *Trichoplusia ni* granulosis virus (TnGV) occlusion bodies, from the granulin fraction of *Heliothis armigera* granulosis virus occlusion bodies or from the polyhedron fraction of nuclear polyhedrosis viruses. The invention embraces baculovirus coded proteins capable of degrading specific glycoproteins of the peritrophic membrane (PM) and destroying the structural integrity of this membrane in *Trichoplusia ni* larvae. These baculovirus enhancing proteins (subgroup B of genus Baculovirus) are characterized by molecular weights of about 101 and about 104 Kd and by being free from occlusion bodies (OBs) and other viral particles.

DETAILED DESCRIPTION OF THE PREFERRED EMBODIMENT

Nuclear polyhedrosis viruses (family: Baculoviridae) are rod-shaped, enveloped particles containing a double-stranded, closed circular DNA genome. It is well-established that members of subgroup A of baculoviruses generate two distinct phenotypes which are involved in causing disease in susceptible lepidopteran hosts such as the cabbage looper, *Trichoplusia ni*. The occluded virus form derives its envelope in the nucleus prior to occlusion in proteinaceous occlusion bodies. This is the primary phenotype responsible for the horizontal transmission of the virus in insect populations. The occluded viruses are released from the protein matrix upon contact with the alkaline midgut fluid of a feeding larva following ingestion of occlusion bodies. The virions released from the occlusion bodies infect midgut columnar cells and initiate the infection cycle.

Prior to the infection of midgut cells of a larval host, the virions released from occlusion bodies in the midgut lumen must survive the alkaline digestive fluids and pass through a peritrophic membrane which lines the midgut lumen. The peritrophic membrane is a noncellular tube comprising primarily of proteins, chitin, and glycosaminoglycans. It is generally nonporous to particles larger than 20 nm and is believed to serve as a barrier to invading microorganisms. Within the occlusion bodies of *Trichoplusia ni* granulosis virus (TnGV), Applicant has found at least two virus-coded proteins with enzymatic activity which degrade specific glycoproteins of the peritrophic membrane of *Trichoplusia ni* larvae, viz., glycoproteins with molecular weights of 253, 194 and 123 Kds, thereby changing the structure and presumably the permeability of the peritrophic membrane. Virus enhancing factors with similar characteristics have also been found in occlusion bodies of *Autographa californica* nuclear polyhedrosis virus and *Heliothis armigera* granulosis virus (HaGV).

VIRUS ENHANCING PROTEIN FACTORS

To purify the *T. ni* granulosis virus occlusion bodies from infected larvae, the larvae were homogenized in water, filtered through 4 layers of cheesecloth, and the occlusion bodies were pelleted for 10 minutes at 8000 g for nuclear polyhedrosis viruses and 25 minutes at 12,000 g for granulosis viruses. After treatment with 1% SDS (w/v) for 30 minutes at room temperature, the occlusion bodies were pelleted and washed three times in water.

$1.7 \times 10^{12}$ *T. ni* granulosis virus occlusion bodies were then dissolved in 1 ml 0.05M sodium carbonate for 15 minutes at room temperature, and layered on a 20% sucrose cushion in water and centrifuged for 45 minutes at 126,000 g at 4° C. The granulin fraction remained on top of the sucrose cushion and was collected. After an incubation of 5 hours at 28° C., the granulin fraction was applied onto a SEPHACRYL S-200 SUPERFINE, a general purpose gel filtration medium with a wet bead diameter of 40–105 μm prepared by covalently cross-linking allyl dextran with N,N'-methylene bisacrylamide to give a rigid gel with a carefully controlled range of pore sizes; (Pharmacia) column (2.6×34 cm) and eluted with 50 mM TRIS HCl [Tris (hydroxymethyl) aminomethane]. pH 7.0, 0.1M NaCl at 1.5 ml/min, and the absorption of the eluate measured at 280 nm. The fractions were collected and tested for the presence of enzymatic activity. The virus enhancing proteins in the fractions were analyzed on a sodium dodecyl sulfate (SDS) polyacrylamide gel. Protein concentrations of the fractions were determined.

CHARACTERIZATION OF THE ENZYMATIC PROPERTIES OF THE VIRAL ENHANCING PROTEINS

The temperature optimum was determined by incubating the viral enhancing proteins and the peritrophic membrane at different temperatures for 5, 15 and 30 minutes, respectively. Enzyme-inactivating temperatures were determined by heat treatment of the viral enhancing protein for 30 minutes at 50°, 60°, 70°, and 80° C., and for 10 minutes at 95° C. The pH optimum of the enzyme reaction was studied by using various dilutions of the viral enhancing proteins in buffers ranging in pH from 6.2 to 10.5. UV inactivation studies were performed by irradiating a viral enhancing protein solution up to $8.64\times10^6$ ergs/cm$^2$. The salt optimum was determined by adding sodium chloride to the reaction mixture at a final concentration of 0.1, 0.2, 0.3, 0.4, 0.5, 0.75, 1.0, 1.5 and 2.0M. The following protease inhibitors were tested by addition to a viral enhancing protein-peritrophic membrane reaction mixture: beta-mercaptoethanol and dithiothreitol at 2.5, 10, 20, 40, 80 and 160 mM final concentration; phenylmethenesulfonylfluoride and iodacetate at final concentrations of 0.01, 0.5, 0.1, 0.5, 1, 2 and 5 mM. Ten μl of viral enhancing proteins were treated with 1 unit phospholipase $A_2$, C and D at pH 8.9, 7.3 and 5.6 respectively for 0.5, 1, 2, and 4 hours in an 11 μl incubation mixture. After phospholipase treatment, the pH of the reaction mixture was adjusted to 7.5 and 10 μl of treated viral enhancing proteins were tested. The control experiments were viral enhancing proteins treated with heat inactivated (15 min at 100° C.) phospholipases, and heat inactivated (10 min at 100° C.) viral enhancing proteins incubated with phospholipases. After incubation the viral enhancing proteins were analyzed on SDS polyacrylamide gels.

Using polyacrylamide gel electrophoresis the molecular weight of the viral enhancing proteins were determined on 7.5% gels. The gels were silver stained and glycoproteins were detected by periodic acid schiff (PAS) staining. For the 2D gel electrophoresis the self-digested granulin (5 hours at 28° C.) was separated on a native 7.5% polyacrylamide gel. The gel lane was incubated in 2× lysis buffer (4% SDS, 20 mM Tris-HCl pH 8.0, 2 mM ethylenediaminatetraacetic acid (EDTA)), 20% glycerol. Bromophenol Blue for ½ hour at room temperature and subsequently layered onto the 12.5% SDS polyacrylamide gel. After electrophoresis, the proteins were visualized by silver staining. The 101 and 104 Kd proteins were extracted from a native gel by crushing a gel slice containing both proteins in 1 ml water and incubating for 5 hours at room temperature. The gel pieces were removed by filtering over siliconized glass wool and the sample was dialyzed against water overnight at 4° C. After lyophilization, the proteins were dissolved in 50 mM Tris-HCl pH 7.0, 0.1M NaCl. This sample was then tested for enzyme activity. Controls consisted of gel pieces removed from a different area of the lane. The sample containing the two proteins with molecular weights of about 101 and about 104 Kd exhibited enzyme activity.

The 101 and 104 Kd proteins migrated as one band in a 7.5% native gel. This was confirmed by purification of the proteins from the high molecular weight band from the native gel. The 12.5% SDS polyacrylamide gel showed that the eluant contained purified 101 and 104 Kd proteins. The 2D-gel electrophoresis demonstrated that the proteins were not composed of subunits.

The characteristics of the virus enhancing proteins of *Trichoplusa ni* granulosis virus are summarized in TABLE 1.

Based on the results of a larval bioassay, the proteins were ten times more stable to UV irradiation than the occluded virions. Whereas a dose of $3\times10$ ergs/cm$^2$ resulted in 93% inactivation of occlusion body infectivity, $3\times10$ ergs/cm$^2$ was necessary to inactivate the enzyme activity.

THE EFFECT OF THE GRANULIN FRACTION (101/104 Kd PROTEINS) AND THE POLYHEDRIN FRACTION ON THE INFECTIVITY OF AUTOGRAPHA CALIFORNICA NUCLEAR POLYHEDROSIS VIRUS IN THE 5TH INSTAR TRICHOPLUSA NI LARVAE

The results of three bioassays, conducted with 20 to 30 larvae at each dose, are summarized in TABLE 2. The $LD_{50}$ and $LD_{90}$ for the virus treated larvae were 9 and 141 occlusion bodies, respectivity. The mortalities, recorded when the active granulin was added to *Autographa californica* nuclear polyhedrosis virus occlusion bodies, indicated that receipt of one occlusion body was enough to kill fifth instar larvae. Thus, roughly a greater than 25-fold increase in infectivity was realized by the addition of the granulin fraction containing the 101/104 Kd proteins to the occlusion bodies, even when it was 10 to 100 times diluted. The increase in infectivity which may be realized by the addition of the proteins found in the polyhedrin fraction of AcMNPV or the granulin fraction of HaGV is less than 5 fold.

TABLE 1

Characteristics of the virus enhancing proteins of *Trichoplusa ni* granulosis virus

| | |
|---|---|
| Molecular weight: | 101 and 104 Kd proteins without subunits |
| pH optimum: | pH 8 |
| Temperature optimum: | 50° C. |
| Heat inactivation temperature: | 30 min 80° C. |
| UV inactivation: | $3\times10^6$ ergs/cm$^2$ |
| Salt preference: | 0.2–2.0 M NaCl |
| Inhibited with | 40 mM β-mercaptoethanol |
| | 5 mM dithiothreitol |
| | 1 mM iodoacetate |

Not inhibited by 5 mM phenylmethenesulfonyonlyfluoride
Resistant against alkaline proteases of *T. ni* larvae
Not stained by glycoprotein staining (PAS)
Not inactivated or degraded by phospholipase $A_2$, C or D

TABLE 2

Bioassay of various concentrations of *Autographa californica* occlusion bodies in the presence of the granulin fraction from *Trichoplusia ni* GV at different dilutions, fed to fifth instar *Trichoplusia ni* larvae

| | | % mortality in the presence of | | | | |
|---|---|---|---|---|---|---|
| Expt. | Occlusion Bodies/ larvae | heat inact.[a] gran. fr. | gran.[b] fr. | 10-1 gran. fr. | 10-2 gran. fr. | 10-3 gran. fr. |
| Control[c] | 0 | | 0 | 0 | | |
| 1[d] | 1.12 | 14 | | 73 | | |
| 2 | 5.6 | 45 | 90 | | | 50 |
| 3 | 14 | 61 | 100 | 100 | 80 | |
| 3 | 28 | 64 | | | | |
| 3 | 140 | 100 | | | | |

[a] Granulin fractions were heat inactivated for 10 min. at 100 C.
[b] The amount of granulin in the undiluted sample was comparable with the granulin that can be released from 1.5 × 10 *Trichoplusa ni* granulosis virus.
[c] Control treatments consisting of heat inactivated granulin gave 0% mortality in all experiments.
[d] The granulin fraction used in experiment 1 was concentrated and filtered through an Amicon filter with 50K molecular weight cutoff. Aliquots of granulin fractions from experiments 1 and 2 were tested in an in vitro peritrophic membrane assay and both samples showed peritrophic membrane glycoprotein-degrading activity.
The in vitro assay which was used for virus treatment of isolated PMs in a test tube is as follows: For this assay, peritrophic membranes from 20 to 28 hour old fifth instar larvae are dissected in water, thoroughly rinsed in water, individually placed in a 2 ml Eppendorf tube and incubated with 10 μl of either NPV or GV occlusion bodies (OBs) at the desired concentration and 2.5 μl of 0.2 M sodium carbonate (to dissolve the OBs).
After incubation for 5 or 15 minutes at 28 degrees, the reaction is stopped by removing the membrane from the tube. The peritrophic membrane is rinsed in water and frozen in dry ice until analyzed by gel electrophoresis. Controls consist of treating peritrophic membranes with occlusion bodies in the absence of sodium carbonate and in sodium carbonate without occlusion bodies.
The peptide composition of the peritrophic membranes was determined by SDS-polyacrylamide gel electrophoresis (SDS-page) according to Laemmli, Nature 277, 680–685 (1970).

The baculovirus proteins of the present invention are useful as components of pesticides. They enhance the infectivity of viral pesticides, especially *Autographa californica* nucleus polyhedrosis virus. Viral pesticides containing the novel proteins of the present invention can be mixed with any of a variety of biological pesticides including *Bacillus thuringiensis*, B.T., as well as with chemical pesticides such as Sevin.

The viral insecticides containing the baculovirus proteins of this invention can be applied in any of a variety of ways heretofore used in integrating baculoviruses into pest management strategies. For example, the direct control of outbreak populations of insects involves broadcast application, either from aircraft or with spray equipment. Aerial application is especially useful in viral control of forest pests. For ground application foggers and mistblowers may be used. Other tactics which may be employed include the release of both virus infected and contaminated hosts and the mechanical manipulation of the environment to make the baculovirus more available for host consumption. It is to be understood that the choice of tactical approaches in using baculoviruses as pesticides depends on the dynamics of the host-pest system to be managed and the relative threat of economic damage. It may be possible to intercede with spot inoculation tactics early in the insect's developmental cycle, or in the preceding generation. However, waiting until pest numbers have reached the economic threshold almost certainly will require the use of broadcast application.

What is claimed is:

1. Baculovirus proteins free of occlusion bodies which proteins break down the physical structure of the peritrophic membrane of lepidopterous larvae through the degradation of structural glycoproteins.

2. A polyhedrin fraction isolated from a nuclear polyhedrosis virus and free from occlusion bodies and other viral particles, said fraction being characterized by enhancing the infectivity of nuclear polyhedrosis viruses against: lepidopterous larvae and by breaking down the physical structure of the peritrophic membrane of lepidopterous larvae.

3. Baculovirus proteins free of polyhedrin and granulin proteins and all viral particles, and which degrades specific structural glycoproteins of the peritrophic membrane of *Trichoplusia ni* larvae, said proteins being characterized by having molecular weights of about 101 and about 104 Kd and being resistant to the midgut alkaline proteases of *Trichoplusia ni* larvae.

4. Baculovirus proteins of claim 2 present in the granulin fraction of the *Trichoplusia ni* granulosis virus.

5. Baculovirus proteins of claim 2 present in the granulin fraction of the *Heliothis armigera* granulosis virus.

6. Baculovirus proteins of claim 2 present in the polyhedrin fraction of *Autographa californica* nuclear polyhedrosis virus.

7. Proteins free of occlusion bodies and all viral particles and which degrade structural glycoproteins of the peritrophic membrane of *Trichoplusia ni* larvae characterized by the following properties: Monomeric molecular weights of about 101 and about 104 Kd, pH optimum of 8, temperature optimum 50° C., heat inactivation 30 min. 80° C., UV inactivation $3 \times 10^6$ ergs/cm$^2$, salt preference 0.2–2.0M NaCl, stable in 4M urea; inhibited with 40 mM-β mercaptoethanol, 5 mM dithiothreitol and 1 mM iodoacetate; not inhibited by 5 mM phenylmethenesulfonylfluoride, resistant against alkaline midgut proteases of *Trichoplusia ni* larvae; not stained by glycoprotein staining; and not inactivated or degraded by phospholipase $A_2$, C or D.

* * * * *